United States Patent [19]
Kassis et al.

[11] Patent Number: 5,308,605
[45] Date of Patent: * May 3, 1994

[54] DIAGNOSIS OF TUMORS WITH 5-RADIOIODO-2'-DEOXYURIDINE

[75] Inventors: Amin I. Kassis, Chestnut Hill; S. James Adelstein, Waban, both of Mass.

[73] Assignee: The President and Fellows of Harvard College, Cambridge, Mass.

[*] Notice: The portion of the term of this patent subsequent to Dec. 31, 2008 has been disclaimed.

[21] Appl. No.: 936,562

[22] Filed: Aug. 27, 1992

[51] Int. Cl.$^5$ .............................................. A61K 43/00
[52] U.S. Cl. .......................................... 424/1.1; 600/4
[58] Field of Search .............................. 424/1.1; 600/4

[56] References Cited

U.S. PATENT DOCUMENTS

| | | | |
|---|---|---|---|
| 3,261,747 | 7/1966 | Commerford | 167/51 |
| 5,077,034 | 12/1991 | Kassis et al. | 424/1.1 |
| 5,094,835 | 3/1992 | Kassis et al. | 424/1.1 |

*Primary Examiner*—Robert L. Stoll
*Assistant Examiner*—Lara E. Chapman
*Attorney, Agent, or Firm*—Allegretti & Witcoff, Ltd.

[57] ABSTRACT

A method or the treatment and diagnosis of tumors is disclosed. This method comprises the administration of an effective amount of a radiohalogenated pyrimidine nucleoside to the tumor affected site.

10 Claims, 2 Drawing Sheets

DIAGNOSIS OF TUMORS WITH 5-RADIOIODO-2'-DEOXYURIDINE

This invention was supported under NIH Grant RO1-CA 15523 and the U.S. Government has certain rights to the invention.

FIELD OF THE INVENTION

The present invention relates to methods of treating and diagnosing tumors in mammals. More specifically, the present invention relates to contacting radiohalogenated pyrimidine nucleosides with a tumor affected site, whereupon the tumor affected site is then treated or diagnosed.

BACKGROUND OF THE INVENTION

For a number of years, the scientific and medical communities have been continually exploring the possibility of using radionuclides for cancer therapy. The use of sealed radioactive sources e.g., radium needles and capsules is now commonplace. However, with the exception of a select number of applications, the hopes of employing unsealed sources for the radiotherapy of a neoplastic disease remain largely unrealized. The problem has two components: (a) a scarcity of appropriate radionuclides, and (b) developing appropriate carrier molecules that can (i) bring the radionuclide into the vicinity of cancerous cells and (ii) incorporating the radionuclide into the tumor cells so as to achieve high ratios of the radionuclide between tumor cells and normal tissues.

The biological toxicity of internally deposited radionuclides can be attributed to radiation-induced ionizations and excitations, nuclear recoil, chemical transmutations, and local charge effects. Gamma and x-ray photons, energetic negatrons and positions have (i) a range of action equivalent to many cell diameters, (ii) are characterized by a low linear energy transfer LET and oxygen-dependent biological effects. On the other hand, radionuclides that decay by electron capture (EC) and/or internal conversion (IC) demonstrate an Auger effect in which extremely low energy, i.e. $<1$ KeV, short range electrons are produced which dissipate their energy typically within nanometer distances from the decay site. Consequently, the biological toxicity of these radionuclides resembles that of high LET radiations and is critically dependent on their intranuclear localization. Furthermore, the oxygen enhancement ratios (OER) obtained following their decay are smaller than those seen with x-irradiation and energetic particles.

The Auger-electron-emitting radionuclide investigated most extensively is iodine-125. Because of its predominant IC decay following EC (approximately 93%), this radionuclide is a prolific emitter of Auger electrons. The electrons most frequently produced dissipate their energy in the immediate vicinity of the decaying atom and deposit $10^5$–$10^9$ rad/decay within 20- to-60-nanometer spheres around the decaying atom. The radiotoxicity of this Auger electron emitter was demonstrated following the in vitro incorporation of the thymidine [TdR]analog $^{125}$IUdR into the DNA of dividing mammalian cells. Further in vitro studies indicate that these and other Auger electron emitters have shown a decrease in radiotoxicity when emission occurs at a distance from the nuclear DNA.

5-Iodo-2'-deoxyuridine (IUdR) is a thymidine analog in which the 5-methyl group of thymidine (TdR) is replaced by iodine. IUdR specifically incorporates into DNA during the synthetic phase of the cell cycle. Most DNA incorporated IUdR is retained for the life of the cell or its progeny. In contrast, the unincorporated IUdR is rapidly catabolized to iodouracil and/or dehalogenated while its half-life in circulation is very short, i.e. less than five minutes in humans and less than seven minutes in a mouse. The preparation of this compound as well as the iodinated $^{123}$I and $^{125}$I versions are fully described in U.S. Pat. No. 4,851,520 the teachings of which are incorporated herein by reference.

Briefly, 2'-deoxyuridine (0.50 g, 2.20 mmol) is dissolved in 2 ml water and the solution is heated to 50° C. To this solution, mercuric acetate (0.74 g, 2.32 mmol) in 3 ml of water is added. The reaction is allowed to proceed for 2.5 h at 50° C., the vial cooled down to 40° C., and sodium chloride (0.32 mg, 5.45 mmol) in 1 ml of water is added. The reaction mixture is stirred for 1 h, and the suspension is filtered, washed and dried.

To 6 mg (8.6 μmol) of the thus prepared 5-chloro-2'-deoxyuridine, 4 mg of Iodogen (9.3 μmol) and sodium $^{123}$I/$^{125}$I]iodide [1–10 mCi) in 0.3 ml of water are added. The mixture is stirred in a closed 2-ml reaction vial at room temperature for 2 h, filtered through a 0.22 μm Millex filter, and injected into the HPLC (C$_{18}$ column). Fractions from the peak with a retention time (R$_T$) of 7.1 min (corresponding to that of an authentic cold IUdR sample) are pooled, the eluant (H$_2$O/C-H$_3$OH,80/20 by volume) evaporated, and the $^{123}$IUdR or $^{125}$IUdR resuspended in saline and sterilized e.g., by filtration, prior to administration into the mammals.

Despite the fact that various pharmaceuticals that exhibit high in vitro toxicity to mammalian cells have been identified over the years, none of these have demonstrated any "magic bullet" characteristics in vivo. To facilitate targeting of tumors, investigators have relied on the direct introduction of the therapeutic/diagnostic agents either into the target area or into an arterial blood supply that immediately precedes the target. Inherent to the absolute success of such approaches are four main assumptions:

1. the target is approximately within an area that can be easily accessed;
2. once within the vicinity of the tumor-containing tissues, the agent (a) freely diffuses throughout all the tissues, (b) is innocuous outside the cell, and (c) is selectively taken up either passively or actively and indefinitely retained by each and every cancerous cell but not by noncancerous cells;
3. once the agent has diffused out of the target area, it must either be converted quickly into an inactive, i.e., nontoxic, form and/or be excreted from the body;
4. the biologic behavior of the agent is not altered by repeated injection, i.e., it lends itself to repeat/continuous injections.

SUMMARY OF THE INVENTION

We have found that IUdR is the agent that meets most of the above requirements when it is contacted with tumors. Hereinafter "tumor" refers to any tissue site affected with cancerous cells whether macroscopically observable or not. Being a low-molecular-weight molecule, IUdR diffuses readily within tissues; when radiolabeled with an Auger electron emitter i.e., $^{123}$I, $^{125}$I, $^{124}$I, $^{131}$I, $^{77}$Br, $^{80m}$Br, it is innocuous outside the cell and ineffective at killing cells when within the cytoplasm; it is, for the most part, taken up selectively by dividing cancerous cells located within nondividing cells and is indefinitely retained following DNA incorporation; nondividing cells will not incorporate IUdR into their DNA; most of the IUdR that is not taken up by cancerous cells will be catabolized/dehalogenated rapidly [$t_{\frac{1}{2}}$ of min]and thus will not incorporate into the DNA of distant noncancerous dividing cells; and being a small molecule, IUdR will not induce an antibody response and as such will lend itself to repeated injections/continuous infusion. These characteristics make radiolabeled IUdR desirable for the treatment or diagnosis of tumors whether macroscopically observable or not.

Accordingly, the present invention relates to methods for the treatment of tumors comprising administering a therapeutically effective anti-tumor amount of radiohalogenated pyrimidine nucleosides in a pharmaceutically acceptable vehicle to a tumor affected site. These radiohalogenated compounds include for example, UdR labelled with $^{123}I$, $^{125}I$, $^{124}I$, $^{131}I$, $^{77}Br$, $^{80m}Br$, to form, in particular, radioiodinated pyrimidine nucleosides, such as 5-iodo-2'-deoxyuridine. Additionally, the present invention relates to methods for the diagnosis of tumors comprising administering an effective diagnostic amount of radiohalogenated pyrimidine nucleosides in a pharmaceutically acceptable vehicle to a tumor affected site, and thereafter imaging the tumor scintigraphically. These methods, as well as the pharmaceutical compositions, will become more apparent from the following detailed description.

DESCRIPTION OF CERTAIN PREFERRED EMBODIMENTS

Figure 1:
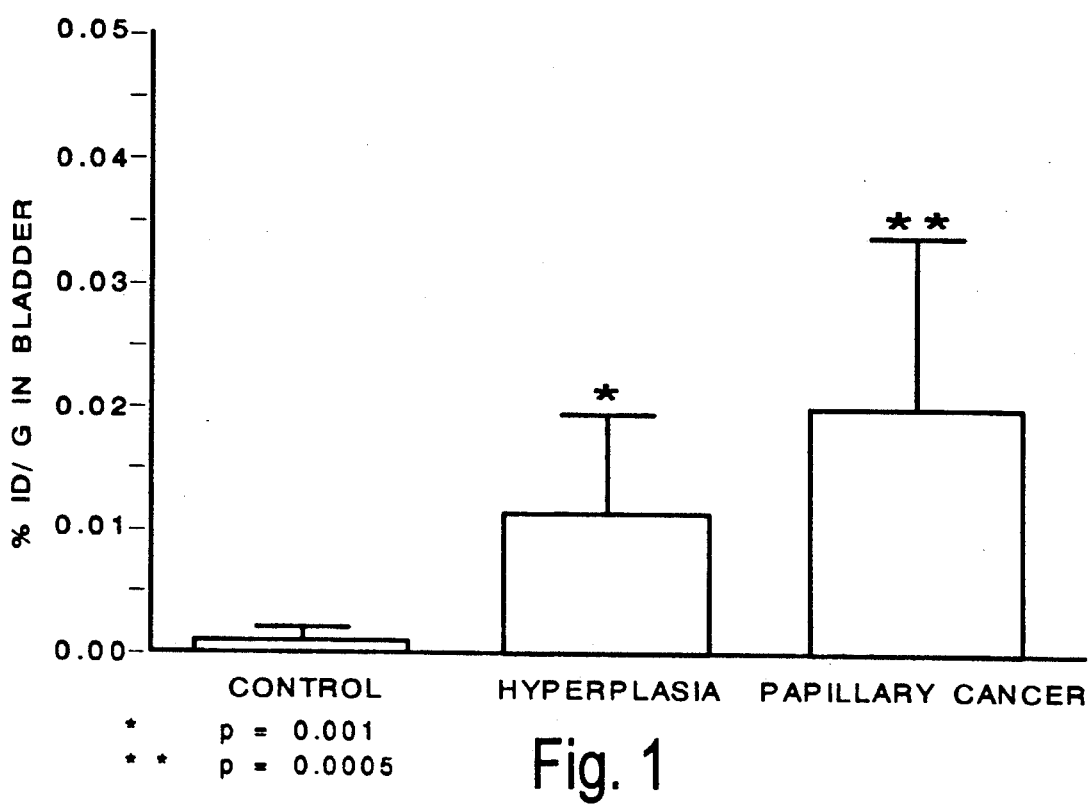
FIG. 1 Percent injected dose per gram of bladder (mean ± standard deviation) 48 h postintravesical administration of [$^{125}I$]IUdR as function of pathology (t-test: * p=0.001; ** p=0.0005).

According to the present invention, the selected radionucleoside e.g., $^{123}$IUdR, $^{125}$IUdR or $^{131}$IUdR prepared according to the method of U.S. Pat. No. 4,851,520, is dissolved in a pharmaceutically acceptable vehicle such as sterile normal saline yielding an effective diagnostic or therapeutic amount per dose unit. Generally speaking, each dose contains about 1-5 mCi, for diagnosis, and 10-500 mCi, for therapy, of the selected compound.

The resulting pharmaceutically acceptable composition may be administered in vivo to several types of tumors, whether macroscopically detectable or not, as follows:

1. For tumors within the bladder wall: The composition is administered directly into the bladder following intubation, or following direct intratumor administration, single/multiple injection or infusion.

2. In ovarian cancers: Following intraperitoneal administration, single/multiple injection or infusion.

3. In intrahepatic tumors: Following initial intraarterial administration via a hepatic artery catheter, single/multiple injection, infusion or vein.

4. Any tumor that is accessible by injection or infusion, whether single or multiple, via intratumor, intraarterial, intraventricular, intrathecal, intralymphatic, intraorgan containing tumor, intratissue containing tumor, intracavity containing tumor e.g., pulmonary, intapleural, organ, organ lining, tissue, bone marrow or other cavities where tumors may be located.

The pharmaceutically acceptable compositions for administration of the radiolabeled IUdR may be formulated by methods known to the pharmacist art, using suitable nontoxic, parenterally acceptable solvent such as normal saline, Ringer's solution and formulating into sterile dosage forms for these administrations.

It is to be understood that the specific dose level and the particular dosage regimen for any particular patient will depend upon a variety of factors including for example, the age, body weight, sex and severity of the particular condition of the host undergoing therapy. The dosage regimen therefore needs to be individualized by the clinician based on clinical response.

In order to illustrate further the practice of this invention, the following examples are included:

EXAMPLES

I. $^{123}$IUdR in the Scintigraphic Diagnosis of Brain Tumors

Exponentially growing 9 L gliosarcoma cells were stereotactically implanted into the right caudate nucleus of 3-week-old CDF (Fisher 344) rats. Briefly, the rats were anesthetized via an i.p. injection of ketamine (40 mg/kg) and xylazine (10 mg/kg) and placed in a small animal stereotactic frame (Kopf Instruments). A sagittal incision through the scalp exposed the skull and a small burr hole was made 1. 3 mm posterior and 4 mm to the right of the bregma. Tumor cells ($2 \times 10^4/10$ $\mu$l PBS), were then injected slowly (within 30 sec) at a depth of 4 mm using a 701 Hamilton syringe. The needle was left in place for 1 min and then withdrawn slowly. The hole was plugged with bone wax and the incision closed. The animals developed sizable tumors (0. 1-4 mm in diameter) within 16 days and died by day 20±2. Control animals were sham-operated with the injection of normal saline.

5-Iodo-2'-deoxyuridine was simultaneously radiolabeled with a mixture of [$^{123}I/^{125}I$]sodium iodide by the method according to U.S. Pat. No. 4,851,520. Briefly, 2'-deoxyuridine (0.5 g, 2.20 mmol) was dissolved in 2 ml water and the solution is heated to 50° C. To this solution, mercuric acetate (0.74 g, 2.32 mmol) in 3 ml of water was added. The reaction was allowed to proceed for 2.5 h at 50° C., the vial cooled down to 40° C., and sodium chloride (0.32 mg, 5.45 mmol) in 1 ml of water was added. The reaction mixture was stirred for 1 h, and the suspension was filtered, washed and dried.

To 6 mg (8.6 $\mu$mol) of the prepared 5-chloro-2'-deoxyuridine, 4 mg of Iodogen (9.3 $\mu$mol) and sodium [$^{123}I/^{125}I$]iodide (1-10 mCi) in 0.3 ml of water were added. The mixture was stirred in a closed 2-ml reaction vial at room temperature for 2 h, filtered through a 0.22 μm Millex filter, and injected into the HPLC ($C_{18}$ column). Fractions from the peak corresponding to that of an authentic cold IUdR sample (retention time=7.1 min) were pooled, the eluant ($H_2O/CH_3OH$, 80/20 by volume) evaporated, and the $^{123}$IUdR/$^{125}$IUdR mixture resuspended in saline and sterilized by Millipore filtration.

$^{123}$IUdR (150–400 μCi $^{123}$IUdR in 10 μl) was stereotactically injected directly into the brain 15 to 17 days post tumor or saline inoculation using the same coordinates used to introduce the tumor cell or normal saline inoculum. Scintigraphic images of $^{123}$IUdR were obtained 1 to 38 h post $^{123}$IUdR injection using a gamma camera (Starcam) equipped with a medium energy collimator (anterior views, 128×128 matrix, 2.67 magnification, 10 min acquisition). Biodistribution of radioactivity was determined 40 h after $^{123}$IUdR injection. The following samples and tissues were removed, rinsed, blotted, weighted, and their $^{123}$I radioactive content determined in a gamma counter: tumor-containing or sham-operated right brain (RB), left brain (LB), frontal lobes (FL), skin (SK), muscle (M), small intestine (SI), large intestine (LI), spleen (SP), liver (L), kidney (K), heart (H), lung (LU), right skull (RS), left skull (LS), bone (BN), thyroid (TH), bladder (B), urine (U), stomach (S), stomach contents (SC), and blood (BD). The frontal lobes were dissected away from the rest of the brain and counted separately. A coronal section of the brain was made through the plane of the injection site, and one-half of this tissue was immediately frozen in isopentane using liquid nitrogen for later sectioning (6 μm) for histopathology and autoradiography. Examination of the other half indicated that in the few instances where the tumor mass was macroscopically visible, its delineation from the normal brain tissue was difficult. For these reasons, this part of the brain was cut in half through the midline to obtain a "right brain" sample (containing the tumor site and/or injection site), and a "left brain" sample (uninjected side representing the activity in the contralateral "normal" brain).

The scintigraphic images obtained 1 h after $^{123}$IUdR injection showed activity in the head of both tumor-bearing and sham-operated control animals. Activity in the stomach and the bladder was also evident suggesting the rapid dehalogenation and excretion of free iodine. No activity was seen in the thyroid (0.1% potassium iodide solution had been added to the drinking water 48 h prior to the administration of radioactive IUdR). Images obtained at subsequent intervals (12–38 h) demonstrated clearance of the activity from the head of all control animals by 12 h and persistence of the activity within the same region in all tumor-bearing animals. Bladder and stomach activities were still observed in both groups.

Regions of interest were drawn around the head of all animals. Even 1 h after injection, the mean counts per pixel in the tumor-bearing animals were at least twice that of the control animals. This ratio increased with time to a maximum of 3.8 by 38 h.

Figure 2:
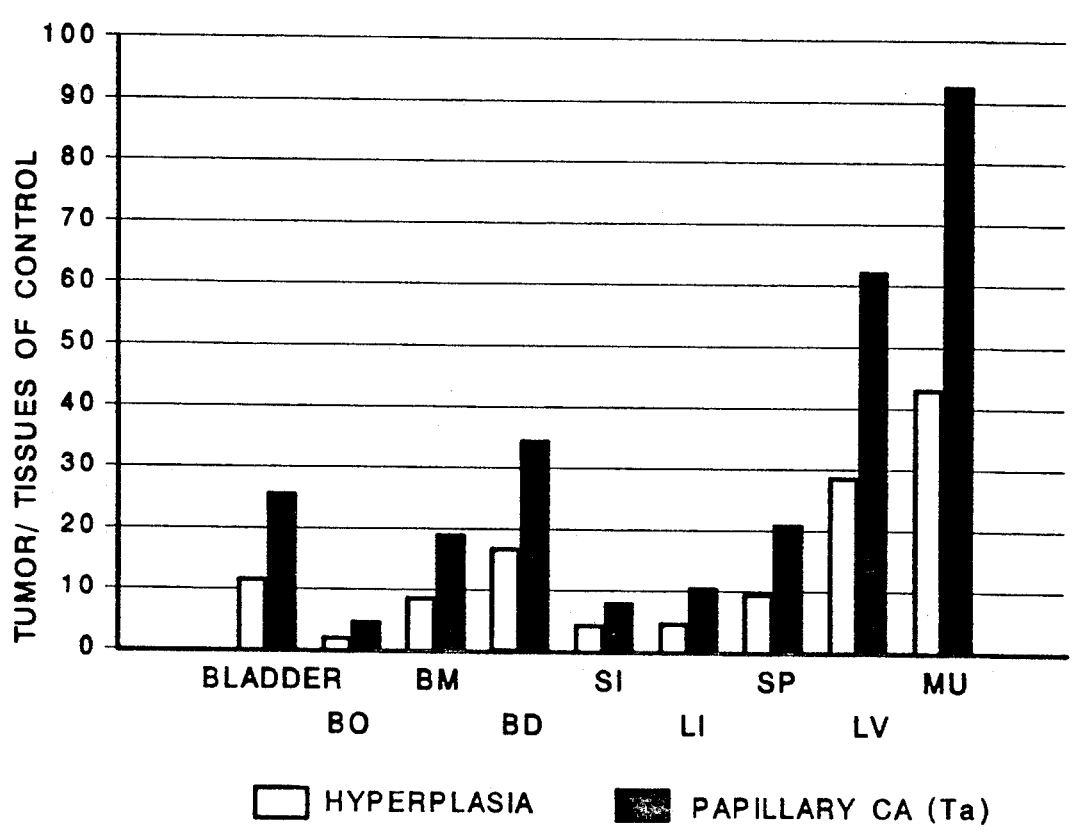
FIG. 2 Tumor to normal tissue ratios 48 h postintravesical administration of [$^{125}I$]IUdR (BO=bone, BM=bone marrow, BD=blood, SI=small intestine, LI=large intestine, SP=spleen, LV=liver, mu=muscle).

To further illustrate applicants' methods of treating and diagnosing tumors, the teachings and figures described in U.S. Pat. Nos. 5,077,034 and 5,094,835 (the incorporated patents) and having incorporated by reference and will be referred to below. Biodistribution data taken 40 h after $^{123}$IUdR injection indicated that samples obtained from the "left brain" (uninjected side) or the frontal lobes in tumor-bearing and control animals had similar amounts of activity (FIG. 2 of the incorporated patents). On the other hand, samples obtained from the "right brain" (injected side) in tumor-bearing animals contained 0.36±0.14% of the injected dose per gram (%ID/g, mean±SD) as opposed to 0.09±0.02% ID/g from the same side of the brain in sham-operated controls ($P<0.05$). Since a large proportion of the weighed "tumor" sample is, in fact, uninvolved brain tissue (some of the tumors were not visible macroscopically at the time of dissection, i.e., <0.5 mm in diameter), these % ID/g values underestimate the actual tumor uptake. This is further emphasized by the high uptake that was observed in two animals, one in which 12% of the injected dose was found to be associated with a tumor that could be precisely excised, and another in which 25% of the injected dose was found in a tumor that occupied a large portion of the "right brain" specimen. As suggested by the scintigraphic studies, the activity in all other normal tissues was low with the exception of the stomach and the bladder. However, examination of these organs indicated that the high activities observed were mainly associated as indicated in FIG. 2 of the incorporated patents with the stomach contents and with urine.

Figure 3:
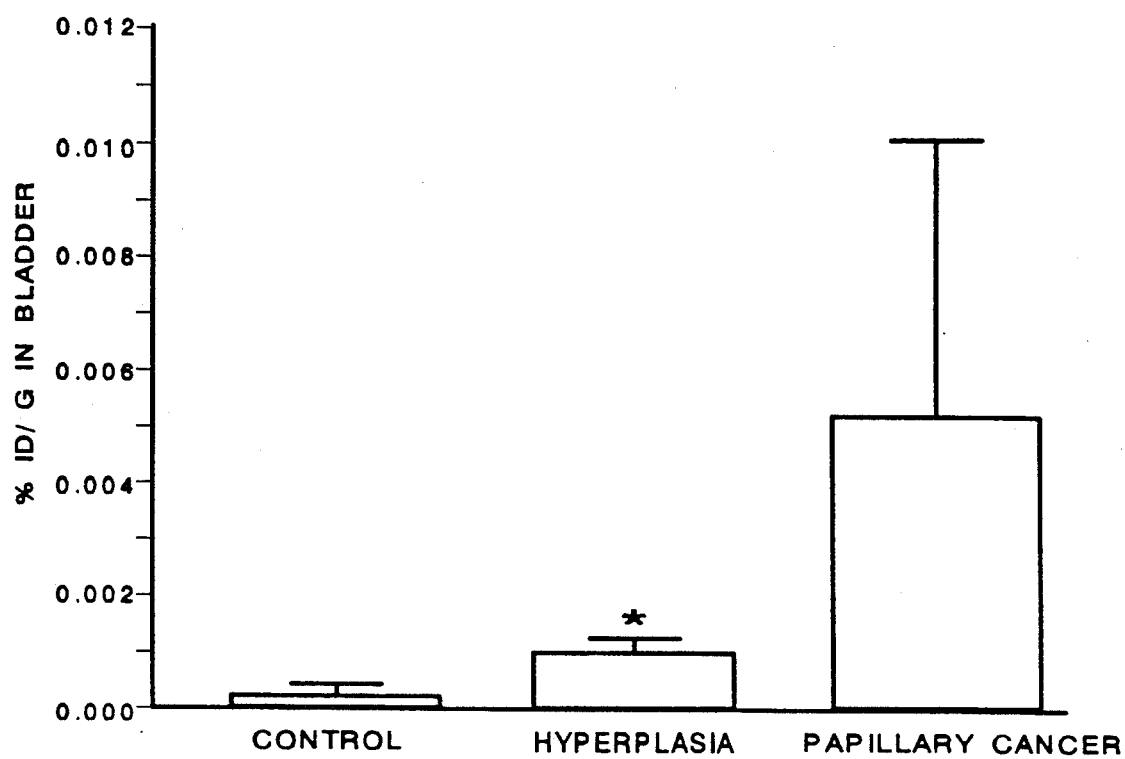
FIG. 3 Percent injected dose per gram of bladder (mean ± standard deviation) 1 week postintravesical administration of [$^{125}I$]IUdR as function of pathology (t-test: * p=0.002).

Biodistribution data shown in FIG. 2 of the incorporated patents was used to calculate, tumor to normal tissue ratios [FIG. 3 of U.S. Pat. No. 5,094,835] which were found to be equal to or greater than eight for all the tissues. Particularly interesting ratios were right brain/left brain=22, right brain/frontal lobes=71, right brain/blood=9. Again, much higher tumor to normal tissue ratios (range of 53 to 488) were obtained in an animal where the brain tumor mass was sufficiently large (about 3×4 mm) to be excised and where the radioactivity per gram of tumor could be accurately assessed.

II. Therapeutic Efficacy of $^{125}$IUdR and $^{123}$IUdR in Ovarian Tumors

1. Intraperitoneal Injection of $^{125}$IUdR and $^{123}$IUdR leads to High Tumor to Noutumor Ratios: The murine ovarian tumor (MOT) used in these experiments arose spontaneously in the ovary of a C3H mouse and is maintained in our laboratories by serial intraperitoneal (i.p.) transplantation in female C3HeB/FeJ mice. We have examined the appropriateness of the i.p. route for IUdR administration as a means to (i) bypass the rapid intrahepatic dehalogenation of this agent, and (ii) obtain high tumor to nontumor ratios. In these experiments, mice were injected with $10^6$ tumor cells 24 h prior to the i.p. administration of $^{125}$IUdR (5 injections, 4 h apart). Biodistribution studies 24 h following the last $^{125}$IUdR injection have shown extremely favorable tumor to non-tumor ratios [FIG. 4 of the incorporated patents. Tumor-to-normal-tissue ratios derived from the biodistribution results ranged from 20 for organs with actively proliferating cells (for example uterus, intestine, stomach) to over 400 for organs with nondividing cells (brain, heart).

Analogous results were obtained from the scintigraphic images acquired 1, 2, 16 and 24 hr following a single injection of 300 μCi $^{123}$IUdR (FIG. 5 of the incorporated patents). At 1 h post radiopharmaceutical injection, focal localization of radioactivity was observed in the abdomen of both tumor-bearing mice and control animals. However, at later time points, the focal area of abdominal activity persisted only in MOT-bearing mice while it cleared from the abdomen of animals without tumor, confirming biodistribution results.

2. $^{125}$IUdR Is an Effective Antineoplastic Agent In A Mouse Ascites Tumor. The tumor used in these experiments is the same murine ovarian tumor described above. We have determined the median survival of mice after i.p. challenge with various tumor cell inocula. The results indicate that the median survival of these mice is proportional to the number of tumor cells inoculated into the mice.

The relatively long survival of tumor-bearing mice facilitates quantitative evaluation of tumor cell killing after treatment with $^{125}$IUdR and can be used to calculate a cellular survival fraction. We have, therefore, studied tumor cell survival as a function of the dose of $^{125}$IUdR administered i.p. at 4 h intervals beginning 24 h after tumor cell i.p. inoculation ($10^5$-$10^6$ cells). Because IUdR dehalogenates rapidly in vivo, potassium iodide is added to the animals' drinking water to block thyroid uptake of the released radionuclides.

When mice are treated with four doses of $^{125}$IUdR at 4-h intervals and the survival fraction plotted as a function of the dose per treatment, a rapid decrease in the tumor cell survival fraction ($10^{-3}$) is observed at doses of 20 μCi per treatment with the curve being flat at higher levels (FIG. 6 of the incorporated patents). When seven consecutive injections of $^{125}$IUdR are given, a similar steep reduction in tumor cell survival is also observed; the plateau in this regimen occurs at a survival fraction of $10^{-5}$. Finally, treatment with equivalent doses of IUdR radiolabeled with $^{131}$I (a negatron emitter whose decay is not associated with any significant yield of Auger electron emissions) does not result in any decrease in survival.

3. $^{123}$IUdR Is An Effective Antineoplastic Agent In A Mouse Ascites Tumor. Recently, we have repeated the experiments described above using $^{123}$IUdR (5 i.p. injections, 4 h intervals, 24 h post i.p. tumor inoculation). Our results indicate that the incorporation of this Auger electron emitter into the DNA of these tumor cells also prolongs median survival of the tumor-bearing animals (FIG. 7 of the incorporated patent) in a dose-dependent fashion. When the survival fraction of tumor cells is plotted as a function of dose, an exponential decrease is obtained similar to that observed with the $^{125}$IUdR data (FIG. 8 of the incorporated patent).

4. [$^{125}$I/$^{131}$I]]IUdR Is An Effective Agent In The Detection And Diagnosis Of Bladder Cancer.

No carrier added [$^{125}$I/$^{131}$I] IUdR was synthesized as described previously, see U.S. Pat. No. 4,851,520 hereby incorporated by reference, and purified on a C$_{18}$ reverse phase HPLC column. The radiochemical purity of the product was >99% as determined by TLC with specific activities of 81.40 TBq/mmol and 96.94 GBq/mmol for [$^{125}$I] IUdR and [$^{131}$I] IUdR, respectively.

TUMOR MODEL

The carcinogen N-methyl-N-nitrosourea (MNU), known to induce transitional cell carcinoma of the bladder, was instilled directly into the bladder lumen of 4-to-5-week old female Fisher 344 rats (20 animals) via bladder catheterization using a 22-gauge angiocatheter (1.5 mg/0.15 ml saline intravesically, every other week for a total of 4 doses). The drinking water was supplemented with a combination of trimethoprim-sulfamethoxasole, neomycin sulfate and polymixin B. Twelve to sixteen weeks after the last MNU infusion, the bladder was catheterized and emptied and [$^{125}$I/$^{131}$I ]IUdR (6.4 to 10.9 MBq [$^{125}$I]IUdR [172 to 294 μCi] and 10.7 MBq [$^{131}$I ]IUdR [290 μCi]) was administered through the catheter in a 100- or 200- μl volume and left in place for 2 h. The bladder contents were then withdrawn and the bladder rinsed with normal saline (5×1-ml). Nontumor-bearing control rats (16 animals) were injected by the same route with identical amounts of [$^{125}$I/$^{131}$I]IUdR. The drinking water of all animals was supplemented with 0.1% potassium iodide from 48 to 72 h prior to the administration of the radiopharmaceutical up to the time of sacrifice. The tumor-bearing rats and the non-tumor bearing control rats were divided into Group A consisting of 12 tumor-bearing and 12 control rats, and Group B consisting of 8 tumor-bearing and 4 control rats. Group A was sacrificed 48 hours after administration of the radiopharmaceutical while Group B was sacrificed one (1) week after administration of the radiopharmaceutical.

Pathologic examination of the bladders of animals subjected to the carcinogen MNU revealed two stages of the disease: seven (7) animals from Group A exhibited hyperplastic changes and ten (10) animals from Group B exhibited papillary carcinomatous changes. Several animals also presented additional squamous metaplasia. Three (3) of the animals exhibited no evidence of tumor and were excluded as were two (2) which exhibited active infection because of uptake of radiolabeled IUdR by proliferating bacteria which spuriously elevated the radioactive content of the bladder. These latter animals also frequently developed stones and calcifying and/or ossifying fibrosis of the bladder wall.

SCINTIGRAPHY

Planar scintigraphic images were obtained with a GE Camstar gamma camera at 4 hours, at 3 days and at 7 days after administration of [$^{131}$I]IUdR (ME collimator, anterior views, 256×256 matrix, 20% window, 5-min acquisition, 2.0 magnification). [$^{131}$I]IUdR was used for imaging because of its longer half-life compared to [$^{123}$I]IUdR (8 days vs 13.2 h) which permitted imaging at later time points, i.e., after the metabolism of radiolabeled IUdR had occurred and the radiolabeled metabolites and/or free iodide had been excreted.

Planar scintigraphic images obtained on day 3 following intravesical administration of [$^{131}$I]IUdR demonstrated the virtual absence of activity in normal animals while the only visible area of activity remaining in the tumor-bearing animals was over the region of the bladder. Similar activity persisted on Day 7.

BIODISTRIBUTION

The biodistribution studies were conducted at 48 hours and at 1 week after administration of radiolabeled IUdR in order to quantitate the in vivo distribution of the radiopharmaceutical in terms of percent injected dose per gram of tissue (%ID/g) and to derive tumor to normal tissue ratios. Various organs and tissues of interest were excised, rinsed, blotted dry, weighed, and their radioactive content was determined in a gamma counter along with that of urine, stomach contents, blood and bone marrow.

Data, as indicated in FIG. 1, was derived from the study conducted after 48 hours. The data indicates a significant difference in the percent injected dose per gram (%ID/g) in the bladder of tumor-bearing animals as compared to the control group. At the time of the biodistribution studies it was noted that all the tumor-bearing animals had evidence of bilateral hydronephrosis (with wide communication between the bladder and the ureters). This complication, which seldom occurs in bladder cancer patients, contributed to the systemic distribution of the radiopharmaceutical. In the control group on the other hand, most of the intravesical radiolabeled IUdR solution remained with the bladder and permeation to the systemic circulation was very low, limited to normal diffusion and/or effects of possible minimal trauma to the bladder wall secondary to the catheterization procedure. In order to obtain a better assessment of the expectations in humans where the delivery of the radiopharmaceutical would be well controlled and confined to the bladder, we expressed the target to nontarget ratios as the quotient of the activity observed in the bladder of the tumor-bearing animals to that of the normal tissues of the control animals. These ratios are indicated in FIG. 2 and are all above 1 for tissue groups BO=bone, BM=bone marrow, BD=blood, SI=small intestine, LI=large intestine, SP=spleen, LV=liver and MU=muscle. The ratios range in the hyperplasia group from 2.0 bone) to 43.2 (muscle), the normal bladder being 12.2, and in the papillary carcinoma group from 4.4 (bone) to 92.5 (muscle), the normal bladder being 26.2.

The data of FIG. 3 was derived from the study conducted after one (1) week. The data as compared with the data of FIG. 1 indicates a significant difference in the percent injected dose per gram in the bladder of animals with hyperplasia (Group A, p=0.002) but not with papillary carcinoma (Group B, p=0.104) compare to the control group. This may be due to the wider variation observed within this group and to the fact that, within one week, a significant shedding of the papillary carcinomatous urothelium may have taken place thereby eliminating a significant portion of cells that had taken up radiolabeled IUdR.

Figure 4:
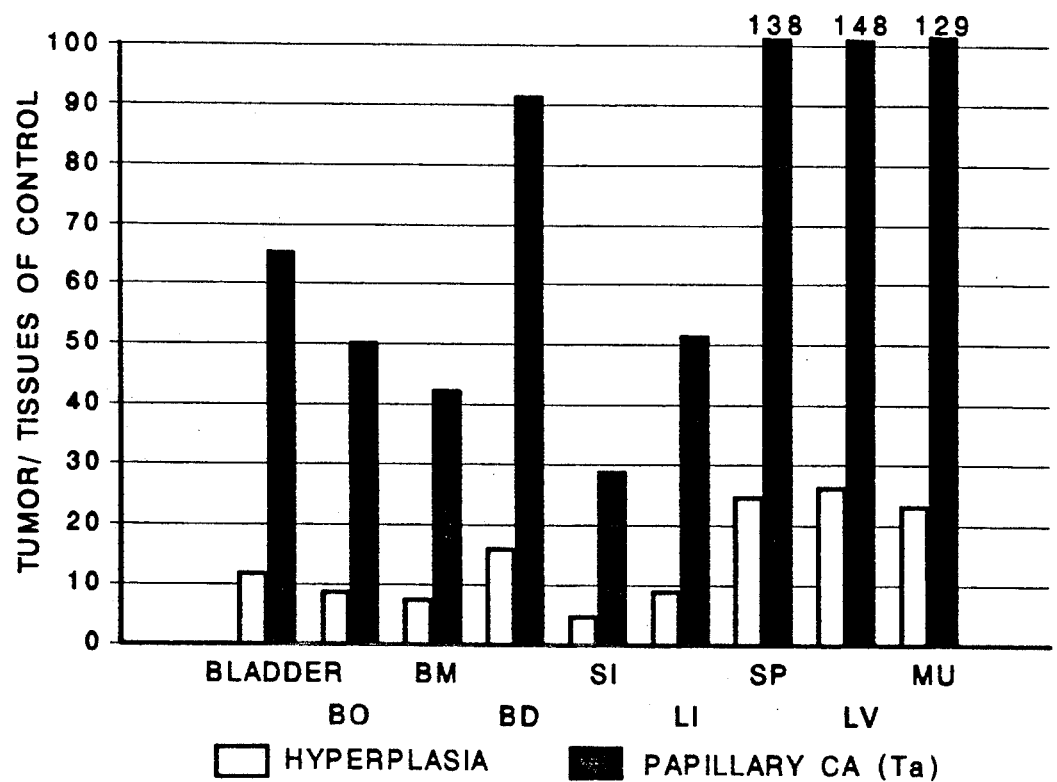
FIG. 4 Tumor to normal tissue ratios 1 week postintravesical administration of ($^{125}I$]IUdR (BO=bone, BM=bone marrow, BD=blood, SI=small intestine, LI=large intestine, SP=spleen, LV=liver, NU=muscle).

The quotient of the activity observed in the bladder of group A to that of the normal tissues of the control animals as indicated in FIG. 4 were all above one (1) ranging from 5.0 (small intestine) to 147.7 (liver), the normal bladder being 65.7.

AUTORADIOGRAPHY

The specificity of targeting and the DNA-incorporation of [$^{125}$I]IUdR were determined by microautoradiography. The distribution and frequency of grains were assessed over the entire section and compared to the histopathologic findings. At the time of the biodistribution studies, the small intestine and the large intestine were quickly frozen in isopentane and liquid nitrogen. Bone marrow smears were fixed in 100% methanol. After rinsing with normal saline, the bladder was fixed in situ with 10% buffered formaldehyde, excised, and subsequently embedded in paraffin. The tissues were then sectioned (5-7 μm thickness), fixed (except for the bladder sections already fixed in vivo) and processed for autoradiography as were the bone marrow smears.

The tissue sections and bone marrow slides were coated with NTB2 emulsion (Kodak) and stored desiccated at 4° C. in light-tight boxes. After various times of emulsion exposure (up to 7 months), the autoradiographic slides were developed for 3 min in D-19 developer (Kodak) and fixed for 5 min in D-11 fixer (Kodak). Finally, the tissue sections were washed in distilled water, stained with hematoxylin/eosin, dehydrated, cleared, and mounted in Permount. Bone marrow slides were stained with Giemsa stain. Tissue and bone marrow slides were then examined under light microscopy.

The autoradiographic studies confirmed the biodistribution data by demonstrating uptake of radiolabeled IUdR by the tumor at the early stage of tumor development, i.e. the hyperplasia stage, as well as in the later papillary carcinoma stage. The normal urothelium was generally free of silver grains. In some tumor-bearing animals, labeling of one or two seemingly normal urothelial cells was observed; however, the DNA incorporation by abnormal urothelium was always significantly higher and control animals did not show uptake in the urothelium. Uptake was also observed in the basal layer of squamous metaplasia and in bacteria when active infection was present, however these latter animals were excluded from the study. Animals with infection/inflammation demonstrated the potential for radiolabeled IUdR to penetrate deep within the bladder wall since incorporation in inflammatory cells and newly formed capillary endothelial cells was seen deep within the stroma.

Autoradiographic studies of normal tissue sections developed serially over time (up to 4 months of exposure) did not show the presence of silver grains associated with actively dividing normal epithelia such as small and large intestine. Of particular interest for therapeutic purposes, bone marrow smears were also free of cell-associated silver grains indicating that stem cells did not incorporate radiolabeled IUdR into their DNA.

It is to be understood that the embodiments of the invention which have been described are merely illustrative of some applications of the principles of the invention. Numerous modifications may be made by those skilled in the art without departing from the true spirit and scope of the invention.

What is claimed is:

1. A method for the diagnosis of tumors in a live mammal comprising administering a diagnostic amount of a radiohalogenated pyrimidine nucleoside directly into a cavity containing a tumor affected site, and thereafter imaging the tumor affected site scintigraphically.

2. The method of claim 1 wherein said radiohalogenated pyrimidine nucleoside is in a pharmaceutically acceptable vehicle.

3. The method of claim 2 wherein said radiohalogenated pyrimidine nucleoside is 2'-deoxyuridine labeled with a radiohalogen selected from the group consisting of $^{123}$I, $^{124}$I, $^{125}$I, $^{131}$I, $^{77}$Br and $^{80m}$Br.

4. The method of claim 3 wherein said diagnostic amount is 1 to 10 mCi of 5-[$^{123}$] iodo-2'-deoxyuridine or about 5 mCi of 5-[$^{131}$] iodo-2'-deoxyuridine.

5. A method for the diagnosis of tumors in a live mammal comprising administering a diagnostic amount of 5-[$^{123}$I]iodo-2'-deoxyuridine or 5-[$^{131}$I]iodo-2'-deoxyuridine in a pharmaceutically acceptable vehicle to a tumor affected site by injection into a cavity containing the tumor affected site, and thereafter imaging the tumor affected site scintigraphically.

6. A method for the treatment of tumors in a live mammal comprising administering an antitumor effective amount of a radiohalogenated pyrimidine nucleoside directly into a cavity containing a tumor affected site.

7. The method of claim 6 wherein said radiohalogenated pyrimidine nucleoside is in a pharmaceutically acceptable vehicle.

8. The method of claim 7 wherein said radiohalogenated pyrimidine nucleoside is 2'-deoxyuridine labeled with a $^{123}$I or $^{125}$I or other radiohalogens.

9. The method of claim 8 wherein said antitumor effective amount is about 10–500 mCi per dose.

10. A method for the treatment of tumors in a live mammal comprising administering an antitumor effective amount of 5-[$^{123}$I]iodo-2'-deoxyuridine or 5-[$^{125}$I]iodo-2'-deoxyuridine in a pharmaceutically acceptable vehicle to a tumor affected site by injection into a cavity containing the tumor affected site, thereafter imaging the tumor affected site scintigraphically.

* * * * *